(12) United States Patent  (10) Patent No.: US 8,428,719 B2
Napadow  (45) Date of Patent: Apr. 23, 2013

(54) SYSTEMS AND METHODS FOR RESPIRATORY-GATED AURICULAR VAGAL AFFERENT NERVE STIMULATION

(75) Inventor: Vitaly Napadow, Chelsea, MA (US)

(73) Assignee: The General Hospital Corporation, Boston, MA (US)

( * ) Notice: Subject to any disclaimer, the term of this patent is extended or adjusted under 35 U.S.C. 154(b) by 44 days.

(21) Appl. No.: 13/260,866

(22) PCT Filed: Mar. 30, 2010

(86) PCT No.: PCT/US2010/029221
§ 371 (c)(1),
(2), (4) Date: Sep. 28, 2011

(87) PCT Pub. No.: WO2010/114836
PCT Pub. Date: Oct. 7, 2010

(65) Prior Publication Data
US 2012/0035680 A1  Feb. 9, 2012

Related U.S. Application Data

(60) Provisional application No. 61/166,606, filed on Apr. 3, 2009.

(51) Int. Cl.
*A61N 1/00* (2006.01)

(52) U.S. Cl.
USPC .......................................................... 607/17

(58) Field of Classification Search ...................... 607/17
See application file for complete search history.

(56) References Cited

U.S. PATENT DOCUMENTS

| 5,458,625 | A | 10/1995 | Kendall |
| 2004/0254612 | A1 | 12/2004 | Ezra et al. |
| 2006/0122675 | A1 | 6/2006 | Libbus et al. |
| 2007/0179557 | A1 | 8/2007 | Maschino et al. |
| 2008/0015642 | A1 | 1/2008 | Johnson et al. |

OTHER PUBLICATIONS

The International Search Report and Written Opinion as mailed on Oct. 20, 2010 for International Application No. PCT/US2010/029221.

*Primary Examiner* — George Manuel
(74) *Attorney, Agent, or Firm* — Quarles & Brady, LLP (57) ABSTRACT

Neurostimulation is provided to afferent nerve fibers of an auricular vagal nerve of a patient. The neurostimulation is harmonized with the pulmonary activity of the patient. In one implementation, a neurostimulation is gated to a portion of the respiratory cycle. For example, the auricular vagal nerve may be stimulated at the end of exhalation. In another implementation, a stimulation regiment to multiple electrodes are harmonized with pre-selected triggers within the respiratory cycle to achieve selective stimulation and/or bilateral stimulation.

20 Claims, 6 Drawing Sheets

SYSTEMS AND METHODS FOR RESPIRATORY-GATED AURICULAR VAGAL AFFERENT NERVE STIMULATION

CROSS-REFERENCE TO RELATED APPLICATIONS

This application is based on, claims the benefit of, and herein incorporates by reference in its entirety, U.S. Provisional Patent Application Ser. No. 61/166,606 filed on Apr. 3, 2009, and entitled "RESPIRATORY-GATED AURICULAR VAGAL AFFERENT NERVE stimulator," and is a U.S. national phase of PCT International Application No. PCT/US2010/029221, filed on Mar. 30, 2010.

STATEMENT CONCERNING FEDERALLY SPONSORED RESEARCH OR DEVELOPMENT

Not Applicable.

BACKGROUND OF THE INVENTION

The field of the invention relates to systems and methods for providing stimulation of central nervous system tissue, muscles, or nerves, or combinations thereof. More particularly, the invention relates to providing neurostimulation to the vagus nerve and/or its branches to provide therapeutic outcomes, such as the treatment of pain, with signals that are adjusted based on pulmonary activity.

The electrical stimulation of a biological tissue, e.g., a muscle or a nerve, often afferent nerves, to indirectly affect the stability or performance of a physiological system can provide functional and/or therapeutic outcomes, and has been used for activating target muscles or nerves to provide relief for a variety of disorders. Many systems use stimulators (i.e., pulse generators) and electrodes to deliver electrical charge to the target site of the muscle or nerve. For example, electrical stimulation of the vagus nerve (VNS) is a validated, United States Food and Drug Administration approved therapy that has improved the lives of many individuals with epilepsy or depression. For example, VNS has been reported to have improved effects on sleep in epileptic patients, and immunomodulatory effects in depression patients.

VNS has also been used for a multitude of other conditions including overeating and Alzheimer's disease. Recent evidence suggests that VNS may have anti-nociceptive effects, particularly in patients with depression. Animal studies have linked stimulation of vagal afferents with antinociception. Both animal studies and recent human studies, suggest that during active VNS, pro-nociception can occur when stimulus intensity is low (e.g., about 30-60% of pain threshold, or approximately 0.5-2 mA or more or less), but anti-nociceptive effects predominate when stimulus intensity is high (e.g., just below or above pain threshold, or approximately greater than 2.5 mA or more or less). Moreover, chronic VNS (e.g., at mean values of about 0.7 to 1.4 mA) may raise pain thresholds (i.e., analgesia) for both tonic pinch and heat pain, as well mitigating the so-called pain wind-up phenomenon (a phenomenon related to central sensitization) when mechanical stimuli are applied. These results have been promising in terms of analgesia. Moreover, VNS has the advantage of greater side effects tolerance and better patient adherence because the VNS therapy is computer programmed, as compared to pharmacotherapy that requires patient adherence to a drug, e.g., pill regimen.

Unfortunately, classical VNS can also induce morbidity stemming either from co-activation of efferent vagal fibers (e.g., bradycardia, asystole, larynx/pharynx disorders, dysphagia), or from infection or hardware failure due to the invasive nature of VNS systems. VNS systems typically require open surgery to implant one or more electrodes on or near the vagal nerve, and may also include tunneling a lead to connect the electrodes to a pulse generator also implanted under the skin. The application of a less invasive vagus nerve stimulation therapy would allow VNS benefits to reach a larger percentage of afflicted populations.

Therefore, it would be an advance in the art to provide improved systems and methods for delivering electrical stimulation to the vagus nerve and/or its branches.

SUMMARY OF THE INVENTION

The present invention provides systems and methods for providing neurostimulation to the vagus nerve and/or its branches to provide therapeutic outcomes, such as the treatment of pain, epilepsy, depression, overeating, and Alhzeimer's disease with signals that are adjusted based on pulmonary activity. In particular, the systems and methods use a detecting device to detect pulmonary activity over time. A value is calculated based on the detected pulmonary activity over time. This calculated value is then compared to a threshold value that is based on previously detected pulmonary activity. When a predetermined relation, such as a match or within a predefined range is found between the calculated and threshold values, a stimulator is instructed to provide neurostimulation to at least one auricular branch of a vagus nerve. In this regard, the neurostimulation is advantageously correlated to the detected pulmonary activity providing improved therapeutic outcomes.

In one implementation, systems and methods provide respiratory-gated auricular vagal afferent nerve stimulation. The systems and methods include at least one electrode, a stimulation circuit, a detection device, and a controller. In one implementation, a first electrode is adapted to be electrically coupled to a first afferent nerve fiber in a first auricular branch of a vagus nerve of a patient. A second electrode is adapted to be electrically coupled to a second afferent nerve fiber in a second auricular branch of the vagus nerve. The stimulation circuit is connected to each of the first electrode and to the second electrode to deliver a first signal to the first electrode and a second signal to the second electrode, thereby respectively stimulating each of the at least first and second corresponding nerve fibers. The detection device is adapted to detect pulmonary activity of the patient and convert the detected pulmonary activity into a corresponding detection signal for delivery to the controller that is connected to the stimulation circuit. The controller is connected to each of the stimulation circuit and the detection device and is adapted to adjust each of the first signal and the second signal based on the received detection signal.

In another implementation, respiratory-gated auricular vagal afferent nerve stimulation is provided to a patient. Electrical signals are received from a transducer detecting pulmonary activity of the patient. The received electrical signals are compared to a reference threshold value algorithmically determined from previously received electrical signals. Based on the comparison, a stimulation signal is sent to an electrode that is coupled to an auricular branch of a vagus nerve of the patient.

In yet another implementation, systems and methods comprise a detection device adapted to detect pulmonary activity of a patient and convert the detected pulmonary activity into a corresponding detection signal. A controller is connected to the detection device and is adapted to receive the detection signal and to generate an output signal. A stimulation circuit is connected to the controller and is adapted to receive the output signal and to generate a neurostimulation signal. A first electrode is adapted to be electrically coupled to an afferent nerve fiber of an auricular branch of a vagus nerve of a patient, and the stimulation circuit is adapted to deliver the neurostimulation signal to the first electrode for selective stimulation of the nerve fiber to achieve a therapeutic function.

The foregoing and other advantages of the invention will appear from the following description.

BRIEF DESCRIPTION OF THE DRAWINGS

Implementations may become more apparent from the detailed description set forth below when taken in conjunction with the drawings, in which like elements bear like reference numerals.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION

The various aspects of the invention will be described in connection with systems and methods for delivering neurostimulation to an auricular branch of the vagus nerve of a patient through the use of Respiratory-gated Auricular Vagal Afferent Nerve Stimulation (RAVANS). That is because the features and advantages that arise due to the systems and methods are well suited to this purpose. Still, it should be appreciated that the various aspects of the invention can be applied to achieve other objectives as well.

In RAVANS, the electrical stimulation to at least one afferent nerve fiber in an auricular branch of a vagus nerve of a patient may be varied based on the pulmonary activity of the patient. In one implementation, an electrode (e.g., percutaneous, implanted, or surface) is placed in electrical conductive contact (i.e., electrically coupled; the electrode proximity to the excitable nerve fibers allows current flow from the electrode to excite the nerve) with the auricular branch of the vagus nerve, pulmonary activity is monitored in real-time, and preselected characteristics in the pulmonary activity trigger selective neurostimulation of the auricular branch of the vagus nerve.

RAVANS can facilitate minimally or non-invasive isolation of afferent fibers in vagus nerve stimulation thereby reducing deleterious effects due to vagal efferent stimulation. Moreover, RAVANS can reduce infection-associated morbidity typically due to surgical intervention.

RAVANS can provide minimally invasive or non-invasive therapy for various medical conditions including: epilepsy, depression, overeating, Alzheimer's disease, chronic pain, or combinations thereof. Other uses of RAVANS can include: prevention of fatal arrhythmias; improving autonomic balance; restoring parasympathetic/sympathetic tone in hypertrophic cardiac myopathy; increasing coronary blood flow; decreasing anginal symptoms; reducing anxiety disorders; and providing treatments for migraines and fibromyalgia, as non-limiting examples. In some implementations, RAVANS can be utilized to treat Chronic Pelvic Pain (CPP) patients with both low and high psychiatric co-morbidity, a subpopulation which has been notoriously difficult to treat and is in need of new, innovative therapies.

Neurobiology of VNS

Figure 1:
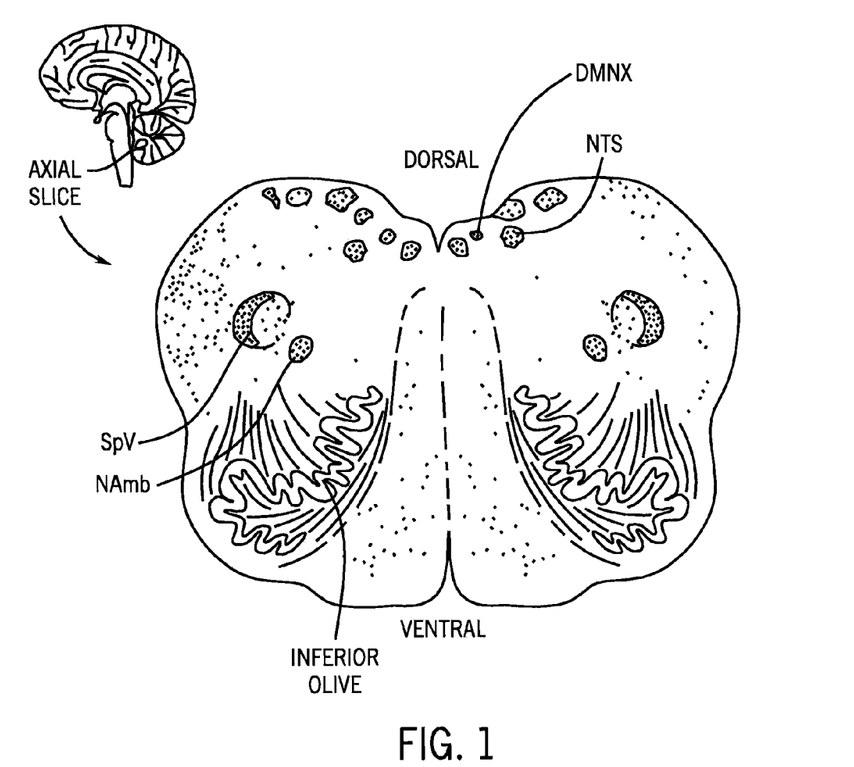
FIG. 1 is a cross-sectional anatomical illustration of a medullary region of a brain.

Referring to FIG. 1, the afferent vagus nerve synapses bilaterally on the Nucleus Tractus Solitarius (NTS) in the dorsal medulla. The NTS sends information to efferent (e.g., premotor) parasympathetic nuclei located in the medulla. These efferent regions include the dorsal motor nucleus of the vagus (DMNX) and the nucleus ambiguus (NAmb), and outflow from these regions course through efferent fibers of the vagus nerve. The NTS also transfers information to the parabrachial nucleus (PBN) in the pons, which then relays signals to the thalamus, hypothalamus, amygdala, and insula (sometimes considered the visceral primary sensorimotor cortex). Moreover, the DMNX, NAmb, and NTS further communicate with a set of brain regions including the Locus Ceruleus (LC, noradrenergic), rostral Ventromedial Medulla (rVMM, serotoninergic), midbrain periaqueductal gray (PAG), hypothalamus, amygdala, and dorsomedial prefrontal and anterior cingulate cortices. Thus, the NTS connects with a diffuse system of brain regions. These limbic and paralimbic brain regions also constitute the Central Autonomic Network (CAN). Neurochemical effects of VNS include increased GABA (an inhibitory neurotransmitter) in the Cerebrospinal fluid (CSF). In summary, this supraspinal network of brain regions may be the mechanistic substrate of VNS therapeutic effects.

VNS can also induce afferent-efferent vagal feedback, wherein stimulation of vagal afferents induces vagal outflow, most likely though NTS/NAmb connectivity. Increased vagal outflow to the heart has been noted through measures of heart rate variability (HRV). Furthermore, increased efferent parasympathetic HRV modulation has also been noted following stimulation of esophageal vagal afferents, further suggesting closed-loop vagal feedback.

Neurobiology and Efficacy of Transcutaneous VNS (t-VNS)

The NTS also receives somatosensory afference along the auricular branch of the vagus nerve (ABV) from specific portions of the pinna (auricle, outer ear). While variability exists, cadaver studies have shown that the cymba concha, anti-helix, and cavum concha were innervated by the ABV in about 100%, 75%, and 45% of ears, respectively (see FIG. 3A). ABV afference is transmitted to the medulla (spinal trigeminal nucleus (SpV) and NTS) by neurons located in the superior (jugular) ganglion of the vagus nerve. Within the NTS, ABV afference is transmitted to the interstitial, dorsal, dorsolateral, and commissural subnuclei, which also receive vagal afference from multiple thoracic organs. ABV afference may also induce several afferent-efferent vagal reflexes. While relatively rare, these include Arnold's cough reflex (incidence of about 2.3-4.2%), ear-gag reflex (about 1.8%), ear-lacrimation reflex (about 2%), and ear-syncope reflex (about 0.6%). Thus, feedback loops, similar to the afferent-efferent vagal feedback loops noted above and to the more extensively studied autonomic baroreflex, may also exist for ABV signaling.

Electrical stimulation of somatosensory vagal afferent receptors in the ear is termed transcutaneous-VNS, or t-VNS. Analgesia can be induced by electrical stimulation of the auricle. While significant inter-subject variability exists, electrical stimulation of the cavum concha (a noted site of ABV receptors) can increase experimental pain threshold by about 30% to about 50% in a subset of patients tested. In addition, electrical stimulation on three points on the auricle (one of which was the anti-helix, noted to be innervated by vagal afferents) has demonstrated analgesia for chronic low back pain, cervical pain, and for acute pain during in-vitro fertilization.

Functional Magnetic Resonance Imaging (fMRI) studies of t-VNS, have demonstrated that this non-invasive procedure modulates limbic brain regions and induces positive effects on mood using an Adjective Mood Scale (AMS). Additionally, some studies have evoked brainstem potentials following t-VNS. These neuroimaging studies have focused on stimulating the tragus (shown in FIG. 3A).

Influence of Respiration on Vagal Physiology

Respiration can modulate activity in both input (NTS) and output (DMNX, NAmb) vagal medullary regions. Inspiration increases venous return to the thorax, which increases arterial pressure, and hence vagal afference to the NTS via aortic and carotid baroreceptors. The NTS then exerts inhibitory GABA-ergic control on NAmb vagal outflow during inspiration. By suppressing tonic NAmb outflow, vagal outflow is diminished during inspiration, leading to a transient tachycardia with every breath. This feedback loop actually functions through both the sympathetic and parasympathetic systems and is termed "respiratory sinus arrhythmia." Hence, the dorsal medullary vagal system operates in tune with respiration.

Somatosensory afference tuned to the respiratory rhythm can also modulate autonomic outflow. For instance, in one study, when stimulation was applied to the arm, gated to respiration, heart rate was found to decrease more substantially than for continuous stimulation at the same location.

An Exemplary RAVANS Apparatus

Figure 2:
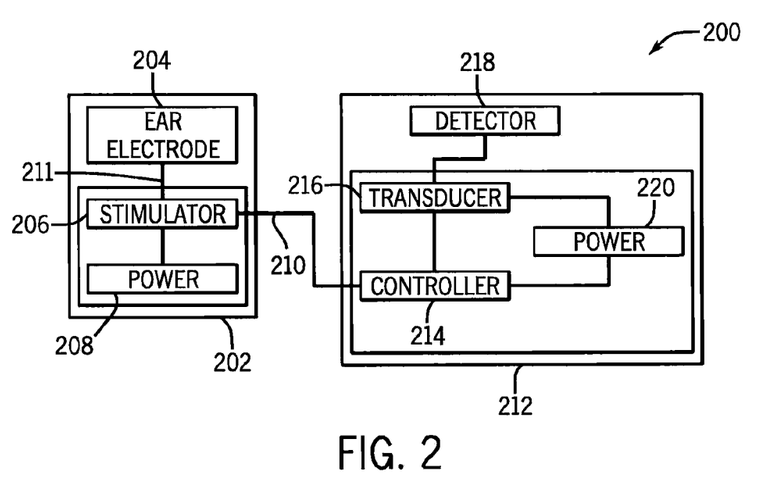
FIG. 2 is a schematic diagram of an exemplary Respiratory-gated Auricular Vagal Afferent Nerve Stimulation (RAVANS) apparatus.

Referring to FIG. 2, a schematic diagram of an exemplary RAVANS apparatus 200 is illustrated. The exemplary RAVANS apparatus 200 includes an ear-based device 202, a pulmonary-based device 212, and a link 210 between the ear-based device 202 and the pulmonary-based device 212. The link 210 can be either wireless (e.g., radio-frequency, RF, Bluetooth) or a wired cable-link. It is to be appreciated that the RAVANS apparatus may have other configurations.

In one embodiment, the ear-based device 202 includes at least one ear electrode 204, a stimulator 206 connected to the ear electrode 204, and a power module 208 connected to the stimulator 206. The ear electrode 204 of the ear-based device 202 may be a percutaneous electrode, i.e., penetrates the skin, or a surface electrode, i.e., placed on the skin. In one implementation, the percutaneous electrode is about 0.1-0.3 mm in diameter and about 2-5 mm in length. The percutaneous electrode 204 may be manufactured from stainless steel or other conductive materials and may have a very fine tip. Alternatively, or in combination, one or more surface electrodes may be used. The surface electrodes may consist of a small disc (e.g., about 2-5 mm diameter) made from a conductive material (e.g., copper) and attached to an adhesive band. Similarly, pre-gelled circular silver/silver chloride electrodes (about 5-10 mm diameter) can be used. It is to be appreciated that a variety of electrode configurations known to one of skill in the art may be used with the RAVANS apparatus 200.

Figure 3A:
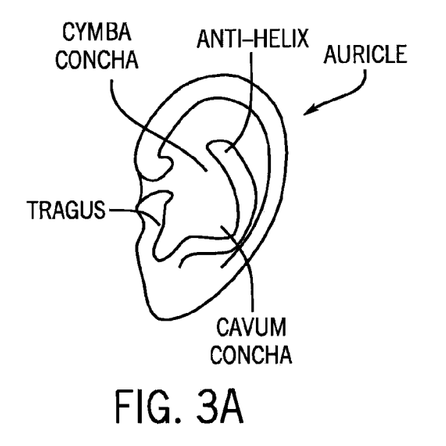
FIGS. 3A and 3B are anatomical views of an auricle showing an exemplary placement of the electrodes in FIG. 2, thereby electrically coupling at least one electrode to an auricular branch of an afferent vagus nerve.
Figure 3B:
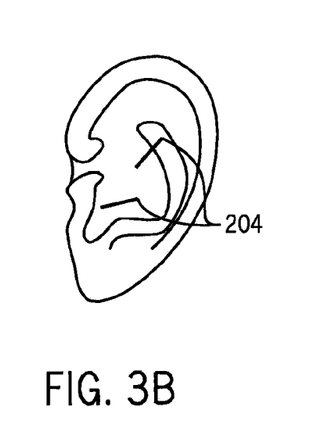

Referring to FIGS. 2, 3A and 3B, a first ear electrode 204 (e.g., anode) can be positioned at a location in or on or near the cavum concha of the auricle (outer ear), while another of the ear electrodes 204 (e.g., cathode) can be positioned at a location in or on or near the cymba concha to serve as the return electrode. It is to be appreciated that the electrode 204 may comprise a multi-contact electrode, e.g., a bipolar electrode. It is also to be appreciated that the return electrode need not be specifically placed in or on or near the cymba concha. Both concha regions have been shown to be innervated by the auricular branch of the afferent vagus nerve. The ear electrode 204 can be connected to the stimulator 206 by a link 211, which may include insulated and shielded (e.g., radio frequency shielded) conductive leads. Alternatively, or in combination, the link 211 may be a wireless connection, such as through radio frequency transponders and receivers.

In some implementations, the stimulator 206 may be housed in an enclosure sized and configured to be placed behind or over the auricle. The auricle itself can be used to physically support the stimulator and power supply for the ear-based device 202. The stimulator 206 may take input from a controller 214 (e.g., a microchip and/or computer) on the pulmonary-based device 212. The stimulator 206 may output its signal to an ear electrode (e.g., either anode or cathode) 204 via insulated and shielded conductive leads, as described above, and receive the return signal via the return electrode.

The stimulator 206 may deliver various electrical signals to the ear electrode 204. In one implementation, the stimulator 206 may deliver a constant-current burst of bi-phasic square-wave pulses at a frequency of about 15-100 Hz, and current intensity set to a moderate-to-strong level (e.g., subjective report by the patient). Each pulse may have a pulse width varying from about 100-1000 microseconds. In some implementations, a total burst duration, following each inhalation and/or exhalation onset, may vary from about 0.5-1.5 seconds. In one implementation, the burst may begin once the stimulator 206 receives a trigger signal (e.g., Transistor-Transistor Logic or TTL) from the controller 214 on the pulmonary-based device 212.

The power module 208 may provide power (e.g., battery) to the stimulator 206 (e.g., about 1.5-9 volts). The power module 208 may be housed, but need not be housed, inside the same enclosure as the stimulator 206 and can be connected to the stimulator 206 with insulated leads known in the art. For example, the power module 208 may include a battery that can be rechargeable, e.g., a recharger may recharge the battery while it remains in the device 202, or the battery may be removed for recharging, depending on specifications and/or applications. The power module 208 may also include or comprise a primary battery, i.e., non-rechargeable battery.

The pulmonary-based device 212 may include the controller 214, a transducer 216, a detector 218, such as a pulmonary activity detector (e.g., a respiratory belt with a strain gage or a nasal air flow detector), and a power supply 220.

According to various implementations, the detector 218 can be a respiratory belt. The respiratory belt 218 may be placed around the rib-cage portion of the thorax. The respiratory belt may be non-elastic and can be made from woven fabric or another material. To illustrate, the respiratory belt may be equipped with a serial pneumatic bellow(s) (where pressure inside the bellows may vary based on lung volume), a strain gage, or a piezoelectric device that is also in serial with the belt fabric, or a combination thereof. The bellows can be made from SILASTIC rubber or similar material. If the bellows are used, a low-compliance TYGON tubing may connect the airspace inside the bellows with the pressure transducer. If the strain gage or the piezoelectric device is used, its output can be connected to the transducer 216 with insulated and shielded conductive leads known in the art.

The transducer 216 may be any electrical, electro-mechanical, photovoltaic or other device that converts one type of energy to another. For example, the transducer 216 may convert either strain (from a strain gage), or air pressure (from bellows or from a nasal air flow detector) into a voltage signal. In one implementation, it may be included with and rest inside an enclosure on the respiratory belt 218, which may also contain the controller 214 or the power supply 220.

The controller 214 may be any device, which includes a computer readable medium including code that, when executed by a processor, performs logical steps. The controller 214 may include circuitry capable of analyzing waveforms, generating a trigger for the stimulator 206, or a microchip with embedded software, as non-limiting examples.

The power supply 220 may provide battery power to the transducer and/or the controller 214 (e.g., about 1.5-9 volts). It may be housed inside the same enclosure as the transducer 216 and the controller 214 and may be connected with insulated leads known in the art. The battery may be rechargeable, e.g., a recharger may recharge the battery while it remains in the device 212, or the battery may be removed for recharging, depending on specifications and/or applications. The power supply 220 may also include or comprise a primary battery, i.e., non-rechargeable battery.

As stated previously, it is to be appreciated that the RAVANS may have other configurations. For example, the power module 208 and the power supply 220 may be in the same device, or may be the same device. Alternatively, or in combination, the stimulator 206 may be housed outside of the ear-based device 202 such as inside the pulmonary-based device 212, for example. The ear-based device 202 may have a pulmonary activity detector, such as when the nasal airflow detector is mechanically linked to a head piece that also houses a portion of the ear electrodes 204.

Figure 4:
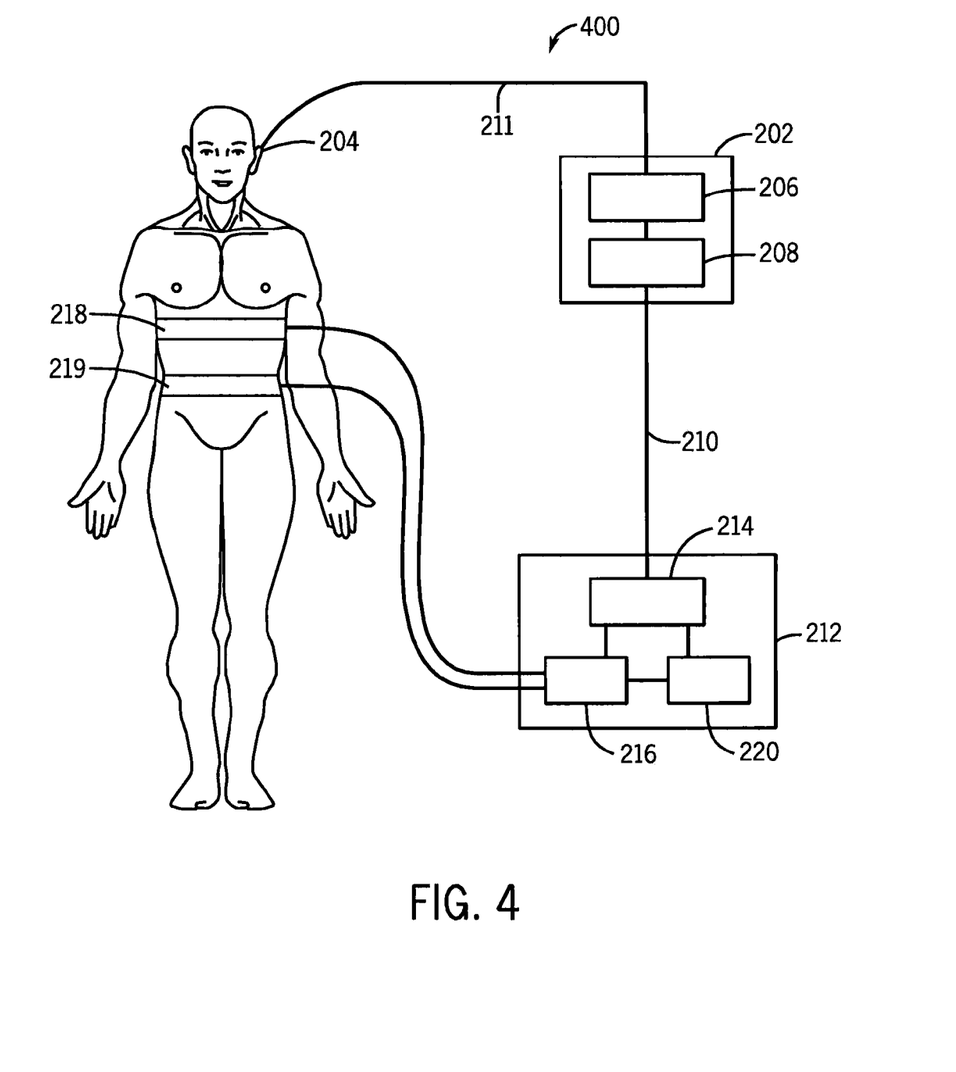
FIG. 4 is a schematic diagram of the RAVANS apparatus of FIG. 2 providing an exemplary neurostimulation regiment to a patient.

Referring to FIGS. 2 and 4, an exemplary RAVANS apparatus 200 is used to provide a regiment of neurostimulation to a patient in a system 400. The patient may lay supine or may recline comfortably in a chair during the therapeutic RAVANS stimulation session. Here, the pulmonary activity detector is shown as a respiratory belt 218 and the ear based device 202 is positioned so as to stimulate the left vagus nerve to limit effects on the heart (the right vagus, which synapses on the sinoatrial node, exerts greater bradycardic effects than does the left vagus, which synapses on the atrioventricular node). Other configurations are also possible. For example, the pulmonary activity detector may be a first respiratory belt 218 worn around the upper chest area and/or a second respiratory belt 219 worn around the abdominal area. If both the first and second respiratory belts 218, 219 are utilizes, an algorithm may combine signals received from each of the respiratory belts to determine an overall respiratory activity of the patient.

Stimulus parameters may vary depending on patient tolerance, but generally, stimulation parameters of approximately 30-90 seconds of stimulation, 20-50 Hz, and about 0.5 mS pulse width burst of stimulation with current amplitude of about 1-3 mA can be applied every about 5-10 minutes throughout portions of the day. In one implementation, the stimulation can be a single burst of about 50 Hz that is given during the expiration cycle of the patient.

Two needles (e.g., sterile, disposable stainless steel silicon-coated filiform needles that are each about 0.16 mm wide and about 1.5 mm long) may be used as the anode and cathode electrodes 204, and may be inserted (or surface mounted) at sensitive (to palpation) points near the ABV, such as on, in, or near the cymba and/or cavum concha of the auricle of a single ear, as shown in FIG. 3B. In another implementation, another pair of needles may be inserted at the cymba and cavum concha of the other ear of the patient for bilateral stimulation of the left and right branches of the ABV. Acupuncture needles may be used for good electrical contact and to apply focal stimulation at the appropriate vagal nerve innervated sites. Corresponding leads 211 may be electrically attached to each of the perspective needles, or the needles may be incorporated into the electrode configuration, as shown.

In another implementation, the stimulator 206 may be a constant-current stimulator, such as a HANS (Han's Acupoint Nerve Stimulator) LH202 (Neuroscience Research Center, Peking University, Beijing, China) that delivers bipolar pulses (pulse width of about 200 us) at about 15 Hz for about 1.5 seconds. Current intensity may be set to achieve moderate to strong (not painful) sensation. The respiratory belt 218 may be pneumatic and placed around the patient's lower thorax to access a respiratory cycle of the patient. For example, the respiratory belt 218 may be attached around the patient's chest and/or abdominal area. The respiratory belt 218 may have low-compliance tubing leading to a pressure transducer (e.g., PX138-0.3D5V, Omegadyne, Inc., Sunbury, Ohio), thereby producing voltage data that corresponds to changes in respiratory volume. The voltage signal from the transducer 216 may be acquired at about 200 Hz by the controller 214, such as a laptop-controlled device (e.g., National Instruments USB DAQCard 6009, 14 bit I/O, with LABVIEW® 7.1 data acquisition software).

Figure 5:
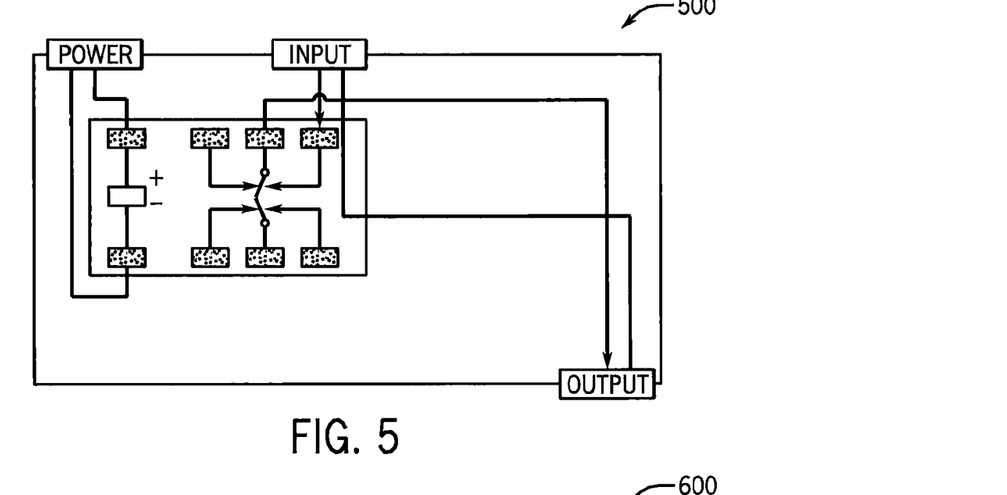
FIG. 5 is a schematic diagram of a high frequency relay that may be used with the RAVANS apparatus of FIG. 2.

The controller 214 may detect different features of the respiratory cycle of the patient. For example, the controller 214 may detect end-inspiration and end-expiration in real-time. Once these temporal landmarks are determined, the code on the controller 214 can be further executed to produce an output, such as a TTL signal, to a high-frequency relay 500 as illustrated in FIG. 5. Examples of such relays in the market place include: G6Z-1P-DC5 or G6J-2P-Y from Omron Electronics Components, Schaumburg, Ill. About one second after the temporal landmark, the high-frequency relay may allow the stimulator 206 to pass current to the ear electrode 204 for about 1.5 seconds during either inspiration, expiration, intermittently, or combinations thereof in a regiment of neurostimulation to the patient.

For example, the controller 214 may acquire the voltage signal from the transducer 216 at a minimum sampling rate of 20 Hz, and analyze this signal in real-time to find when inspiration and/or expiration has begun. The code or algorithm may use a low-pass filtered (cutoff frequency of about 10 Hz) version of the respiratory signal. The average signal may be calculated every about 50 ms. This value may then be compared to a reference threshold that can be defined with an adaptive algorithm based on previous breaths (e.g., the previous five breaths). A separate threshold may be defined for expiration and inspiration. If the current value is greater than the "high" threshold and if the previous landmark was for start-inspiration, then the current value becomes the start-expiration point. This process may continue until the current value is lower than the updating start-expiration point. The same process may be used to find the start-inspiration point, using the "low" threshold instead. The controller 214 may then send a trigger signal to the stimulator 206 (e.g., the ear-based device 202) at a pre-defined lag (e.g., about 0.5-1.0 seconds) from when inspiration and/or expiration has begun. The trigger signal may be a standard TTL pulse.

Use of the RAVANS Apparatus for Treatment of Pain

As stated previously, RAVANS may be used to treat chronic pain. In one implementation, vagal afferent stimulation is supplied to the ABV during select phases of the respiratory cycle (e.g., exhalation) in order to augment the clinical efficacy of t-VNS.

Impact of Psychiatric Co-Morbidity on Chronic Pain

The impact of psychiatric pathology is a salient factor in the treatment of chronic pain, as these patients have a high incidence of psychiatric co-morbidity. Psychiatric pathology amplifies pain perception and diminishes the effectiveness of treatments for chronic pain.

Surveys of chronic pain clinic populations indicate that about 50 to 80 percent of chronic pain patients have significant psychiatric pathology, making it the most prevalent co-morbidity in these patients. In these settings, major depression alone is thought to affect about 30 to 50 percent of patients with chronic pain with anxiety disorders and neuroticism being next most prevalent. Neuroticism can be described as a personality maladjustment wherein patients experience anger, sadness, disgust, anxiety, and a variety of other negative emotions. Fundamentally, depression, anxiety, and neuroticism are disorders of negative affect.

These disorders of negative affect each predict a poor pain and functional outcome in patients with chronic pain, regardless of the treatment modality. As a whole, these studies indicate that it is not the specific qualities of depression vs. anxiety vs. neuroticism, but the overall levels of psychiatric symptoms in these three areas of psychiatric pathology that are predictive of poor outcome. Moreover, patients with chronic pain and psychiatric co-morbidity report greater pain intensity, pain-related disability, and a larger affective component to their pain.

Quantitative Sensory Testing (QST) for Chronic Pelvic Pain (CPP)

A RAVANS regiment to treat chronic pain may, but is not required to include the use of an analgesia outcome measures such as QST evaluations that are taken pre-, post-, or during therapy. Studies have demonstrated that CPP is associated with hyperalgesia (enhanced pain response) at various body sites. Hyperalgesia at local (vulvar) sites has been noted for vulvadynia using both mechanical and heat pain stimuli. However, both mechanical and heat hyperalgesia for vulvadynia, endometriosis, and dysmenorrhea have also been noted at non-local sites such as the occiput, forearm, thumbnail, etc. This seemingly whole-body hyperalgesia suggests that CPP is typically a central pain syndrome.

In some implementations, mechanical QST stimuli may be used to evaluate hyperalgesia and wind-up phenomena in both CPP patients and healthy controls pre-, during, or post-therapy, for example. Repeated mechanical stimuli that produce wind-up (a phenomenon related to central sensitization) and tonic mechanical pain (cuff pressure) can approximate the deep, endogenous pain endemic to CPP patients.

Figure 6:
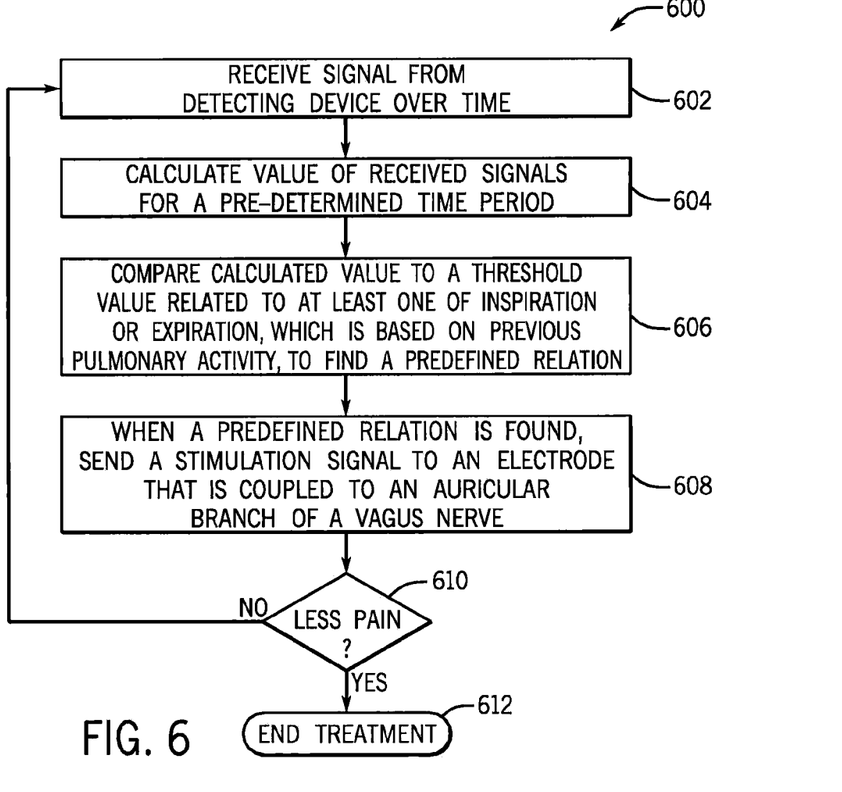
FIG. 6 is a flow chart of an exemplary method for the RAVANS apparatus of FIG. 2 to deliver neurostimulation to an auricular branch of the vagus nerve of a patient.

Referring to FIG. 6, a flow chart illustrates a method 600 to provide neurostimulation to the auricular nerve branch of the vagus nerve of a patient to treat chronic pain. The systems and methods described herein may also be implemented in a bilateral configuration, where neurostimulation is provided to the auricular nerve branch in each ear of the patient. At process block 602, at least one signal is received from a device detecting pulmonary activity over time. For example, one or more respiratory belt(s) 218, 219 may detect pulmonary activity throughout the respiratory cycle of the patient. The detected pulmonary activity at the respiratory belt 218, 219 may be transduced to electrical signals that correspond to changes in respiratory volume. In some implementations, such as at process block 604, an algorithmic value of the received signals for a pre-determined time period is calculated. For example, an average signal may be calculated every about 50 ms to determine a "current signal."

In some implementations, the received signals may also be used to determine threshold values for each of expiration and inspiration in the respiratory cycle of the patient. An adaptive algorithm may calculate the respective thresholds for inspiration or expiration values based on a window of time (e.g., the previous five breaths). For example, a window of five respiratory cycles can be used to define each of the start-expiration threshold and the start-inspiration threshold. Moreover, as the window of five breaths moves, the respective threshold values can be recalculated or updated. Other threshold values may also be algorithmically calculated, such as: mid-expiration or mid-inspiration threshold; maximum-lung volume threshold or minimum-lung volume threshold; or steepest slope in pulmonary activity for either of expiration or inspiration cycles, for example.

At process block 606, the current signal is compared to one or more of the threshold values until a predefined relation is found, such as a signal match(s) or within a predefined range. For example, a match can occur when the current value is lower than the updated start-expiration threshold or when the current value is higher than the start-inspiration threshold. At process block 608, for at least predefined relation current signal, a stimulation signal is sent to at least one ear electrode 204 that is coupled to a corresponding auricular branch of the vagus nerve.

At decision block 610, a determination is made as to whether the level of pain the patient is feeling is past a pre-set pain value (e.g., a "5" in a scale of "1-10" reported pain). For example, the patient may provide a QST evaluation of the pain. If the reported patient pain is higher than the pre-set pain value, the method 600 moves back to the process block 602 for further treatment. Alternatively, if the reported patient pain is lower than the pre-set pain value, the treatment is terminated at a process block 612. In some implementations, the pre-set pain value may be a repeated level of reported pain evaluated after a regiment of RAVANS. For example, the pre-set pain value may be fifty consecutive pain levels of "5" reported after each of fifty regiments of RAVANS.

In some implementations, more than one threshold or value is matched prior to sending of the stimulation signal in the process block 608. For example, if there is more than one ear electrode 204, the stimulation signals to each of the ear electrodes 204 may be harmonized with one another. To illustrate, the regiment of neurostimulation may be set up such that a first ear electrode 204 is set to receive a corresponding set of three stimulation signals after a first start-inspiration threshold is past. Thereafter, the first ear electrode 204 is set to receive a corresponding set of two stimulation signals after a second start-inspiration threshold is past. Moreover, a second ear electrode 204 is set to receive a corresponding set of stimulation signals after the first ear electrode 204 has received the set of two stimulation signals. An optimization algorithm may be used to find an optimum pattern and sequence of stimulation regiments. It is to be appreciated that this configuration is adaptable for multiple stimulating electrodes in a single ear, and for bilateral stimulation with one or more stimulating electrodes in both ears.

Figure 7:
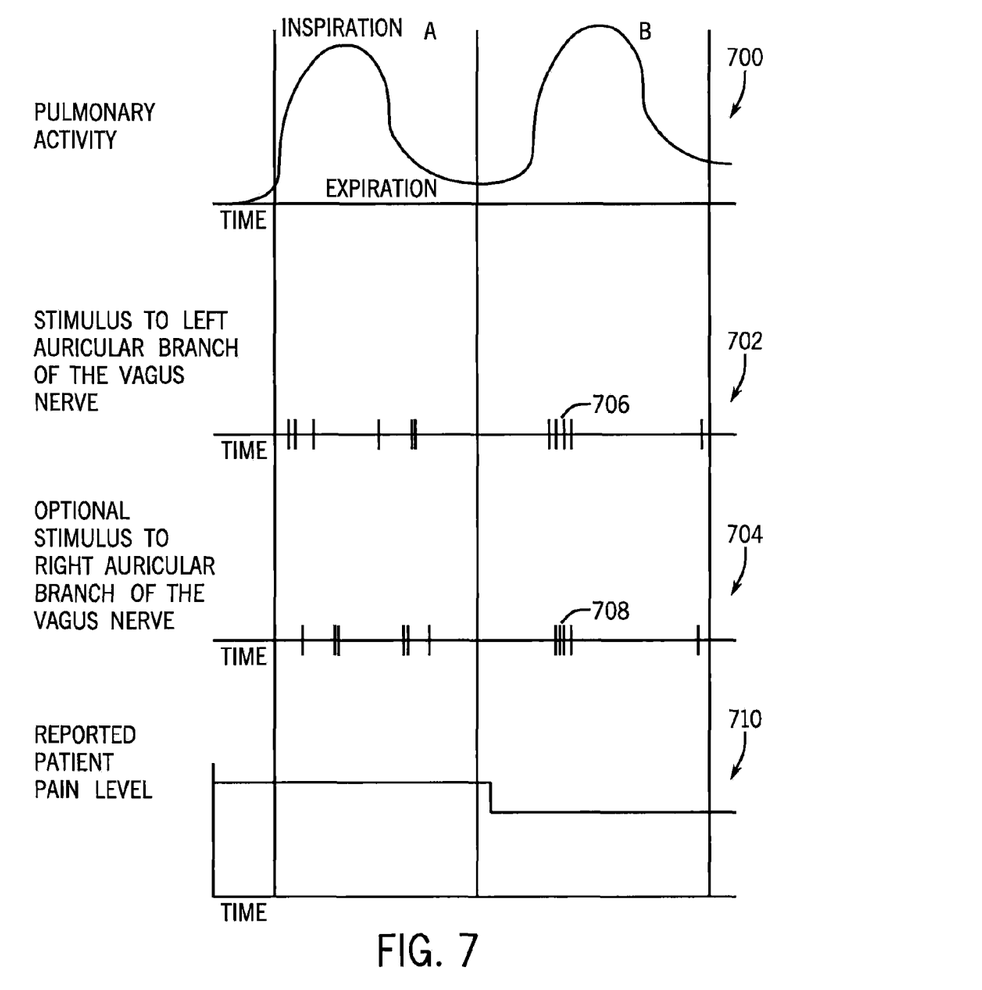
FIG. 7 is a schematic diagram of pulmonary activity showing respiratory cycles of inspiration and expiration that is shown above exemplary electrical signal patterns produced by the RAVANS apparatus in FIG. 2 for each of a left and a right electrode pair electrically coupled to corresponding left and right auricular branches of the vagus nerve, and a reported patient pain level responses to induced pain.

Referring to FIG. 7, a schematic diagram illustrates one representative outcome 700 of the pulmonary activity detector 218 showing respiratory cycles of inspiration and expiration that are shown above electrical signal patterns for each of: a stimulus regiment to a left 702 auricular branch of the vagus nerve and an optional stimulus regiment to a right 704 auricular branch of the vagus nerve. FIG. 7 also illustrates reported patient pain level responses to induced pain 710. Here, the left 702 and right 704 auricular branches of the vagus nerve receive bipolar stimulation that is triggered by various threshold values in the respiratory cycle.

The pattern of the bipolar stimulation may vary between different cycles of the respiratory cycle. In a first respiratory cycle "A," the left 702 auricular branch of the vagus nerve has a stimulation regiment of 2-1-1-2 pattern, while the right 704 auricular branch of the vagus nerve has a 1-2-2-1 pattern. In the second respiratory cycle "B," the left 702 auricular branch of the vagus nerve has a stimulation regiment of 4-1 while the right 704 auricular branch of the vagus nerve also has a 4-1 pattern. However, in the "B" cycle, the stimulation to the right 704 auricular branch has a shorter time interval between stimulations in the initial "4" sets of stimulations. Compare stimulation 706 with stimulation 708. Other stimulation regiments are also applicable. For example, in one implementation, the stimulation regiment can be a single 50 Hz stimulation burst that is administered to the left 702 auricular branch of the vagus nerve during expiration (e.g., a 0.5 sec window of 50 Hz stimulation administered at the end of expiration).

Figure 8:
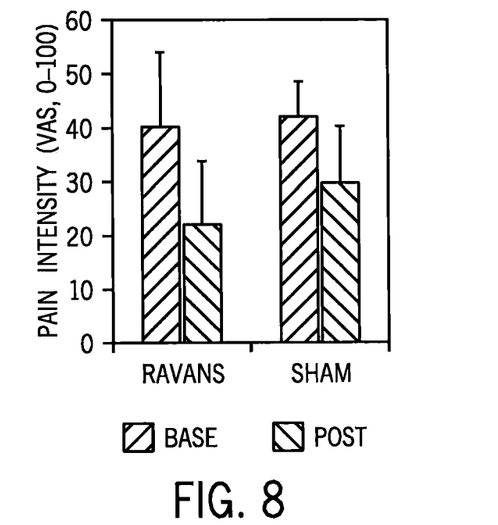
FIGS. 8 and 9 are graphical representations of results using the RAVANS apparatus showing the reduction of pain.
Figure 9:
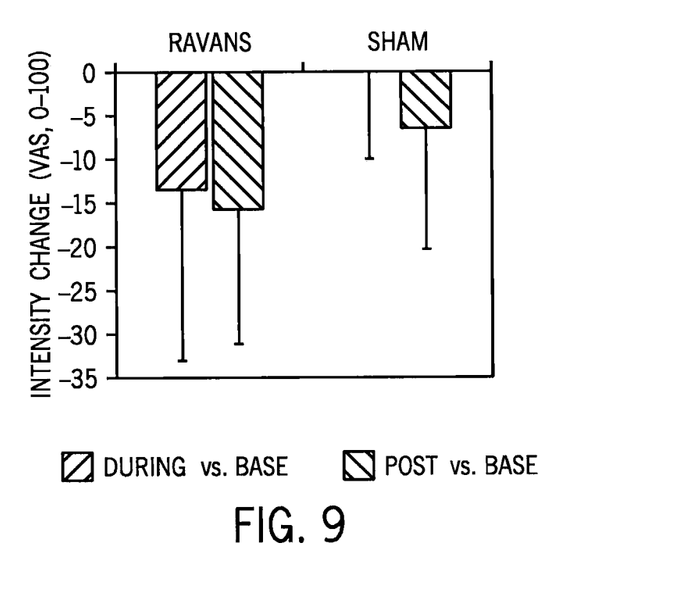

FIGS. 8 and 9 are graphical representations of results using the RAVANS apparatus showing the reduction of pain. Patients were evaluated at baseline, during, and post for both RAVANS and sham therapy, in a randomized crossover design. One evaluation included ischemic cuff pain applied to the gastrocnemius muscle for deep receptor pain, with patients reporting a lower pain intensity with the RAVANS apparatus than with the sham therapy (results shown in FIG. 8). An additional evaluation included windup pain with mechanical probes applied to the dorsal aspect of the finger, with patients reporting a lower change in pain windup intensity than with the sham therapy (results shown in FIG. 9).

For exemplary purposes only, a number of implementations of using the RAVANS to test or treat patients has been described above. In some implementations, a sham RAVANS may be used to collect baseline or control data. For example, a needle may be inserted in a sham location (ear lobe) known to be not innervated by the vagus nerve. All other procedures may be the same, except that stimulation may be delivered either during inspiration or randomly throughout the respiratory cycle, but with similar duration pulses, current intensity, and with the same duty cycle as is done for RAVANS (e.g., about 1 pulse per respiratory cycle).

Implementations have been described in terms of one or more preferred embodiments, and it should be appreciated that many equivalents, alternatives, variations, and modifications, aside from those expressly stated, are possible and within the scope of the invention. The various steps or acts in a method or process may be performed in the order shown, or may be performed in another order. Additionally, one or more process or method steps may be omitted or one or more process or method steps may be added to the methods and processes. An additional step, block, or action may be added in the beginning, end, or intervening existing elements of the methods and processes. Based on the disclosure and teachings provided herein, a person of ordinary skill in the art will appreciate other ways and/or methods for various implements. Moreover, it is understood that a functional step of described methods or processes, and combinations thereof can be implemented by computer program instructions that, when executed by a processor, create means for implementing the functional steps. The instructions may be included in computer readable medium that can be loaded onto a general purpose computer, a special purpose computer, or other programmable apparatus. While the preferred embodiment has been described, the details may be changed without departing from the invention, which is defined by the claims.

I claim:

1. An apparatus comprising:
a first electrode adapted to be electrically coupled to at least a first afferent nerve fiber in a first auricular branch of a vagus nerve of a patient;
a second electrode adapted to be electrically coupled to at least a second afferent nerve fiber in a second auricular branch of the vagus nerve;
a stimulation circuit connected to each of the first electrode and the second electrode to deliver a first signal to the first electrode and a second signal to the second electrode, thereby respectively stimulating each of the at least first and second corresponding nerve fibers;
a detection device adapted to detect pulmonary activity of the patient and convert the detected pulmonary activity into a corresponding detection signal for delivery to a controller that is connected to the stimulation circuit; and
the controller connected to each of the stimulation circuit and the detection device and adapted to adjust each of the first signal and the second signal based on the received detection signal.

2. The apparatus of claim 1, wherein the first auricular branch is a left auricular branch of the patient and the second auricular branch is a right auricular branch of the patient.

3. The apparatus of claim 1, wherein the detection device is a respiratory belt adapted to be worn around the chest of the patient.

4. The apparatus of claim 1, wherein the first electrode is adapted to be non-invasively coupled to the first afferent nerve fiber in the first auricular branch, and the second electrode is adapted to be non-invasively coupled to the second afferent nerve fiber in the second auricular branch.

5. The apparatus of claim 1, wherein the detection signal is an electrical signal.

6. The apparatus of claim 1, further including a transducer adapted to receive the detection signal and convert the detection signal into an electric signal.

7. A method for providing a neurostimulation function comprising:
receiving a signal from a detection device detecting pulmonary activity of a patient;
comparing the received signal to a reference threshold value algorithmically determined from previously received signals to find a predefined relation; and
when a predefined relation is found, sending a stimulation signal to an electrode that is electrically coupled to at an auricular branch of a vagus nerve of the patient to achieve the neurostimulation function.

8. The method of claim 7, wherein the neurostimulation function includes a function selected from a group comprising (i) treatment of epilepsy; (ii) treatment of depression; (iii) treatment of overeating; (iv) treatment of Alzheimer's disease; (v) treatment of pain; (vi) treatment of migraines; (vii) treatment of fibromyalgia; (viii) treatment of angina; (ix) treatment of anxiety disorders; (x) prevention of fatal arrhythmias; (xi) improvement of autonomic balance; (xii) restoration of parasympathetic/sympathetic tone in hypertrophic cardiac myopathy; and (xiii) increase coronary blood flow.

9. The method of claim 7, further including transducing the signal from the detection device into an electrical signal.

10. The method of claim 7, further including generating the reference threshold value by detecting pulmonary activity of the patient over time and calculating the reference threshold value from the detected pulmonary activity.

11. The method of claim 7, wherein the reference threshold value comprises at least one of an expiration reference threshold value and an inspiration reference threshold value.

12. An apparatus comprising:
  a detection device adapted to detect pulmonary activity of a patient and convert the detected pulmonary activity into a corresponding detection signal;
  a controller connected to the detection device and adapted to receive the detection signal and to generate an output signal;
  a stimulation circuit connected to the controller and adapted to receive the output signal and to generate a neurostimulation signal; and
  a first electrode adapted to be electrically coupled to an afferent nerve fiber of an auricular branch of a vagus nerve of a patient, the stimulation circuit adapted to deliver the neurostimulation signal to the first electrode for selective stimulation of the nerve fiber to achieve a therapeutic function.

13. The apparatus of claim 12, wherein the detection signal is an electric signal.

14. The apparatus of claim 12, wherein the therapeutic function comprises the treatment of pain.

15. The apparatus of claim 12, wherein the controller is wirelessly coupled to the stimulation circuit.

16. The apparatus of claim 12, wherein the stimulation circuit is wirelessly coupled to the first electrode.

17. The apparatus of claim 12, wherein the stimulation circuit is housed in an enclosure, and the enclosure is sized and configured to be supported by an auricle of the patient.

18. The apparatus of claim 12, wherein the detection device is a respiratory belt adapted to be worn around the chest of the patient.

19. The apparatus of claim 12, further including a second electrode adapted to be electrically coupled to at least a second afferent nerve fiber in a second auricular branch of the vagus nerve.

20. The apparatus of claim 12, wherein the controller is adapted to receive the detection signal from the detection device and compare the detection signal to a reference threshold value, and to generate the output signal based on the comparison.

* * * * *